Figure 1:
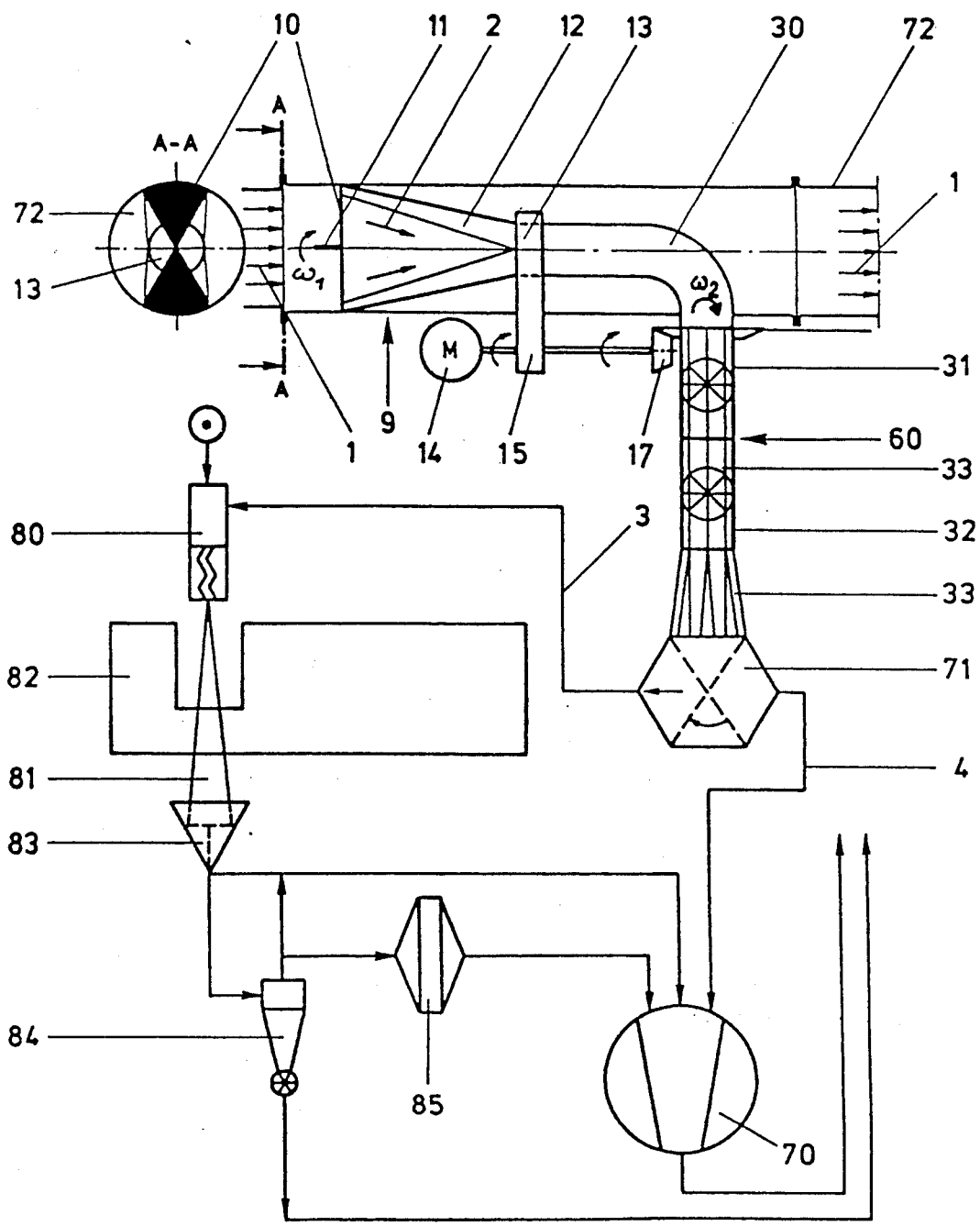

United States Patent [19]
Röthele

[11] Patent Number: 4,946,650
[45] Date of Patent: Aug. 7, 1990

[54] APPARATUS FOR INTEGRATING SAMPLING AND IN-LINE SAMPLE SPLITTING OF DISPERSE PRODUCTS FROM TRANSPORT CONDUITS OR AT FLOW TRANSFER POINTS

[76] Inventor: Stephan Röthele, AM Rollberg 5, 3392 Clausthal-Zellerfeld, Fed. Rep. of Germany

[21] Appl. No.: 423,523

[22] Filed: Oct. 13, 1989

Related U.S. Application Data

[63] Continuation of Ser. No. 304,922, Feb. 1, 1989, abandoned, which is a continuation of Ser. No. 940,065, Dec. 10, 1986, abandoned.

[30] Foreign Application Priority Data

Nov. 12, 1985 [DE] Fed. Rep. of Germany ....... 3543758

[51] Int. Cl.$^5$ .............................................. G01N 1/02
[52] U.S. Cl. ............................... 422/68.1; 73/863.45; 73/863.56; 73/863.58
[58] Field of Search ............................ 422/68, 81, 82; 73/863.45, 863.56, 863.58

[56] References Cited

U.S. PATENT DOCUMENTS

| | | | |
|---|---|---|---|
| 1,646,032 | 10/1927 | Mason | 73/863.56 |
| 2,076,188 | 4/1937 | Thorsten | 73/863.45 |
| 2,547,794 | 4/1951 | Stone | 73/863.45 |
| 3,690,179 | 9/1972 | Olson | 73/863.56 |
| 3,716,167 | 2/1973 | Huntington | 73/863.45 |
| 3,747,622 | 7/1973 | Reinhall | 73/863.45 |
| 3,783,695 | 1/1974 | Grothe et al. | 73/863.56 |
| 4,170,900 | 10/1979 | Ozawa | 73/863.56 |

FOREIGN PATENT DOCUMENTS 1440785 4/1965 France ............................... 73/863.56

*Primary Examiner*—Barry S. Richman
*Assistant Examiner*—Timothy M. McMahon
*Attorney, Agent, or Firm*—Kenyon & Kenyon

[57] ABSTRACT

From a product main flow a sub-flow is withdrawn and from said sub-flow an analysis sample to be analyzed and a remainder obtained by sample splitting. To provide a method and an apparatus for time and space representative sampling and sample splitting to a small analysis sample flow suitable for a following on-line sample analysis the invention provides that sampling and sample splitting are carried out in-line continuously in immediate succession and with the sampling a representative sub-sample flow of up to 1/100 of the product main flow is withdrawn with a sampler head which is arranged rotatably drivably at the inlet of a sampling pipe and the sampling opening of which is at least one circle sector which is rotatable with its tip about the center axis of the product flow transport conduit. The sub-sample flow is continuously split immediately thereafter with a sample splitter by up to three powers of ten. The individual samples produced in the sample splitting are combined individually or in sampling manner with a concentrator such that the subsequent analysis can be carried out immediately on-line without appreciable delaying intermediate storage. Various embodiments of the sampler and sample splitter are explained.

21 Claims, 7 Drawing Sheets

APPARATUS FOR INTEGRATING SAMPLING AND IN-LINE SAMPLE SPLITTING OF DISPERSE PRODUCTS FROM TRANSPORT CONDUITS OR AT FLOW TRANSFER POINTS

This application is a continuation of application Ser. No. 07/304,922, filed Feb. 1, 1989 now abandoned, which is in turn a continuation of Ser. No. 940,065, filed Dec. 10, 1986 and now abandoned.

The analysis of product qualities in production processes takes place in particular in the production of bulk goods with the aid of selected sub-samples which are removed from the process. For the subsequent analyses in the laboratory usually only small sample quantities of a few grams or even milligrams are required so that the problem of removing very small representative analysis sample quantities from large production flows of some tons per hour cannot be solved at all in reproducible reliable manner unless firstly relatively large sub-quantities are removed and thereafter by controlled representative sample splitting the small necessary analysis sample quantities are obtained.

The so-called off-line quality control in disperse products makes available today within a few hours up to a day an analysis result for assessing the product. However, the sampling and sample splitting are generally carried out only at different times and always in rather simple manner. As regards the procedure, reproducibility and systematics they must be considered as by far the weakest point in the information chain to the process in particular also in comparison with the meanwhile available off-line measuring devices, although the first continuously operating samplers are already being introduced, with which however it is not possible to obtain directly any analysis quantities. These samplers would therefore at the most operate quasi-continuously because the requirements of the analyzer following them are transferred to them.

Increasing automation, rationalization and more uniform quality control of product flows make the manual sampling carried out at intervals of time appear extremely dubious, in particular because of its limited representativeness, when the laboratory analyses are carried out with highly accurate measuring devices. The characterization of disperse product properties by at least quasi-continuous particle size analysis, for example with a laser diffraction spectrometer, has meanwhile made this discrepancy particularly noticeable.

The development step to on-line production control with the objective of controlling the process requires after all a sampling interface with which it is possible within a short time for example of a few minutes to have available a small analysis sample quantity which is not only representative but is also quantitatively suitable for the analysis.

A systematical classification of conceivable types of sampling for disperse products must distinguish between production processes in which the product can be present in a fluid carrier medium flow, which may be wet (water) or dry (air), or is transported as separated carrier-medium-free bulk material as occurs for example following a cyclone, mill, classifier, bunker or the like, and is discharged from a transport conduit or a fall shaft or from a conveyor belt or transferred for further processing.

The known samplers such as pipette, plunging or sample siphon, dip samplers, sampling valves, stationary suction probes, sampling lances, sample strippers, pendulum samplers, sampler tubes with half-open slit-like opening or conveyor screws, which in each case only cover a small part of the cross-sections of the production flow to be measured, are not suitable for the complex tasks in on-line operation or at the most only suitable to a limited extent.

In the case of belt transfer samplers are known which at the product transfer points, for example the transfer from one conveyor belt to another conveyor belt, as so-called samplers with slit-like inlet openings reciprocate intermittently beneath the product transfer point and represent for this planar linear sampling problem a solution applicable to less demanding uses if the splitting ratio is not greater than 1:100.

In the case of rotational symmetrical process cross-sections as are usual in the transport of disperse or particulate products in a wet or dry transport medium (transport conduits) known intermittently moving or rotating samplers with slitlike inlet opening cannot however be used when high demands are made on the information accuracy.

The invention therefore has as its object to provide a method and an apparatus for sampling from flows of disperse products from transport conduits or at product transfer points and sample splitting to a representative small analysis sample flow suitable for a subsequent on-line sample analysis.

In a method in accordance with the invention for sampling from flows of disperse products from transport conduits or at product transfer points and sample splitting to an analysis sample flow suitable for a subsequent sample analysis, in which a sub-sample is withdrawn from a product main flow and from said sub-sample an analysis sample flow and a residual sub-flow are obtained by sample splitting, the former being suppliable to a sample analysis and the latter being returned to the product main flow or discarded, it is proposed that the sampling and sample splitting are carried out in-line continuously in direct succession and with the sampling a representative sub-sample flow of up to 1/100 of the product main flow is produced and with the subsequent sample splitting a representative splitting of this sub-flow by up to three powers of ten is carried out to produce an analysis sample flow, for which purpose the single sample flows produced in the sample splitting are conducted out individually or combined in sampling manner so that the subsequent sample analysis can be carried out immediately on-line without appreciably delaying intermediate storage.

In an apparatus in accordance with the invention for sampling from flows of disperse products from transport conduits or at product transfer points and sample splitting to an analysis sample flow suitable for a subsequent sample analysis comprising a sampler for sampling from a rotational symmetrical product main transport conduit for obtaining a sub-sample and a sample splitter following said sampler for obtaining from the sub-sample an analysis sample flow which can be supplied directly to an analyzer, it is proposed that in the product flow transport conduit a sampler is provided for recovering from the product main flow a sub-flow amounting to up to 1:100 of the product main flow having a rotationally drivable sampler head at the input of a sampler pipe whose sampling opening has the form of at least one circle sector having an opening angle ($\alpha$) and which is rotatable with the sector tip about the centre axis of the product flow transport conduit, the sampling pipe opens directly into a sample splitter for the splitting of the sub-flow into an analysis sample flow and a residual sub-flow and the sample splitter splits the sub-flow by up to 1:1000 into the analysis sample flow.

To meet the requirements in an on-line operation a continuous and representative sampling of up to 1/100 of the product main flow is carried out in a rotational symmetrical transport cross-section of the production process. By using a circle-sector-shaped sampling opening sweeping radially over the entire transport cross-section it is ensured that all the area components of the transport cross-section are taken into account representatively in the sampling and an adequately large sub-sample (up to 1/100 of the product main flow) is removed in integrating manner so that in the in-line following sample splitter said sub-sample can also be split in a time representative manner in a ratio of up to 1:1000 down to the small analysis sample mass flow necessary for a representative sample analysis. In this manner only the smallest sample flow necessary for the following sample analysis, which may be a grain size analysis, is taken out of the process whilst the remaining residual sub-flow remains directly in the process production flow or product main flow or is returned thereto.

The new method and the corresponding apparatus solve the problem set so that averaged over time from the entire transport cross-section of the product at least one subflow is continuously representatively removed and supplied to the in-line following sample splitting. This is achieved in that the opening cross-section for removing the subflow is adapted both as regards the form and as regards its time location to the local and time sample situation.

Conventional sub-flow sampling methods, such as the suction extraction with probes according to VDI guideline 2066, sample the product flow traversingly in punctiform manner in accordance with a predetermined raster at time intervals controlled by the sample analyzer. This sampling method does not have either a high local resolving power or an informative integration effect as regards the overall transport cross-section because the weighting of the individual sampling points must proceed on the basis of hypothetical assumptions about the quality of the quasistationary incoming flow and the homogeneity of the distribution of the disperse product in the transport cross-section and with respect to time.

The adaptation in form and time for removing the sub-flow from the main flow takes place via a sampling cross-section or a sampling opening whose outer boundaries define a circle sector with the apex or opening angle $\alpha$ which with its sector tip slowly rotates about the centre of rotation lying in the pipe axis of the product main transport flow. The magnitude of the speed of rotation is only selected such that no disturbing reactions on the product flow occur. This makes the sampling representative with respect to the withdrawal cross-section.

The withdrawal ratio obtained of sub-flow to main-flow is $\alpha/360°$. The radius of the circle sector must be at least equal to or greater than the radius of the cylindrical transport conduit for the main flow to ensure that all the area components are completely covered once within one revolution. One complete revolution corresponds to an integration over the entire main flow transport cross-section. The rotational speed must not coincide with any possible fluctuation frequencies of the main flow. The greater the number of integration cycles from which the total sub-sample is formed by summation the higher the reliability thereof in assessing the product flow.

Instead of a single sector of a circle two opposite circle sectors may also be formed as sampling opening. The withdrawal ratio is then $2\alpha/360°$ when the angles are equal or $(\alpha_1+\alpha_2)/360°$ when different sector angles are used.

Near the sector tip, which as described lies at the centre of rotation, because of the dimensions of the inlet opening tending to zero particles may jam. This is avoided by fitting a conical tip which in its circular base is given a magnitude such that the smallest sector opening lying close to the centre of rotation in the tangential direction corresponds to at least ten times the dimensions of the coarsest particle contained in the bulk material.

The conical tip is to be made as steep as the deflection cone on which it is fitted so that the particles impinging directly in the centre can readily be carried away and conductive in representative manner on an average into the mouth opening. For uniform distribution, a screen with large meshes can additionally be provided between the main line and the intermediate piece.

With on-line measuring cycles of about 5 minutes and a measuring time of one minute and continuous sampling on an average sub-quantities from 100 to 200 integration revolutions are obtained when the speed of rotation is up to $\frac{1}{2}$ revolutions per second. Since because of the increase in the edge influences with small angles it is technically not advisable to form the sampling opening with sector apex or opening angles $\alpha$ below 5°, the withdrawn sub-flow should be at least about 1.5% of the product main flow. The necessary continuous reduction to an analyses sample flow is implemented with the immediately following sample splitter. As a guide it may be taken that for on-line analysis between 1% and 0.001% of the product main flow is required and as stated above the sampling can perform the splitting step in the percentage range and the subsequent in-line sample splitting of the sub-flow by corresponding configuration must perform representatively the further reduction by an additional two to three powers of ten. This can be implemented in that the continuous sub-flow removed with the circle sector sampling opening is split into a discrete sequence of sub-flows which as individual flows by selected combination for example of each 8th, 16th or 32nd, etc., individual flow are finally combined to give the analysis sample flow. By the great subdivision into initially hundreds of individual flows and the systematic performance of the sample collection only very small remaining systematic errors are to be expected.

The invention permits direct adaptation of the obtaining of the analyis sample to the measuring ability of the online analysis system for representative assessment of the product or process. The on-line analysis system used thus permits a combination of the process apparatus to be controlled and the analyzer to give a continuously operating system in such a manner that via the function of the system the validity and informativeness of the analysis results is not questionable. In addition a process signal is obtained as continuous time average value. Ergodicity as with group mean value determination is not required, i.e. the removal of individual samples does not require that the sampling rhythm is also stochastic as random process. Ergodicity in the production process is very difficult to check and usually is not present in any case with fluctuating variables and measurement parameters which make an on-line process control or regulation necessary. A sample analyzer which is ready to measure every 10 minutes cannot obtain representative analyis results when every 10 minutes an analysis sample is supplied to it which in its amount only meets the quantity requirement of the analyzer and completely ignores what has happened in the production process between the sampling instants.

Figure 2:
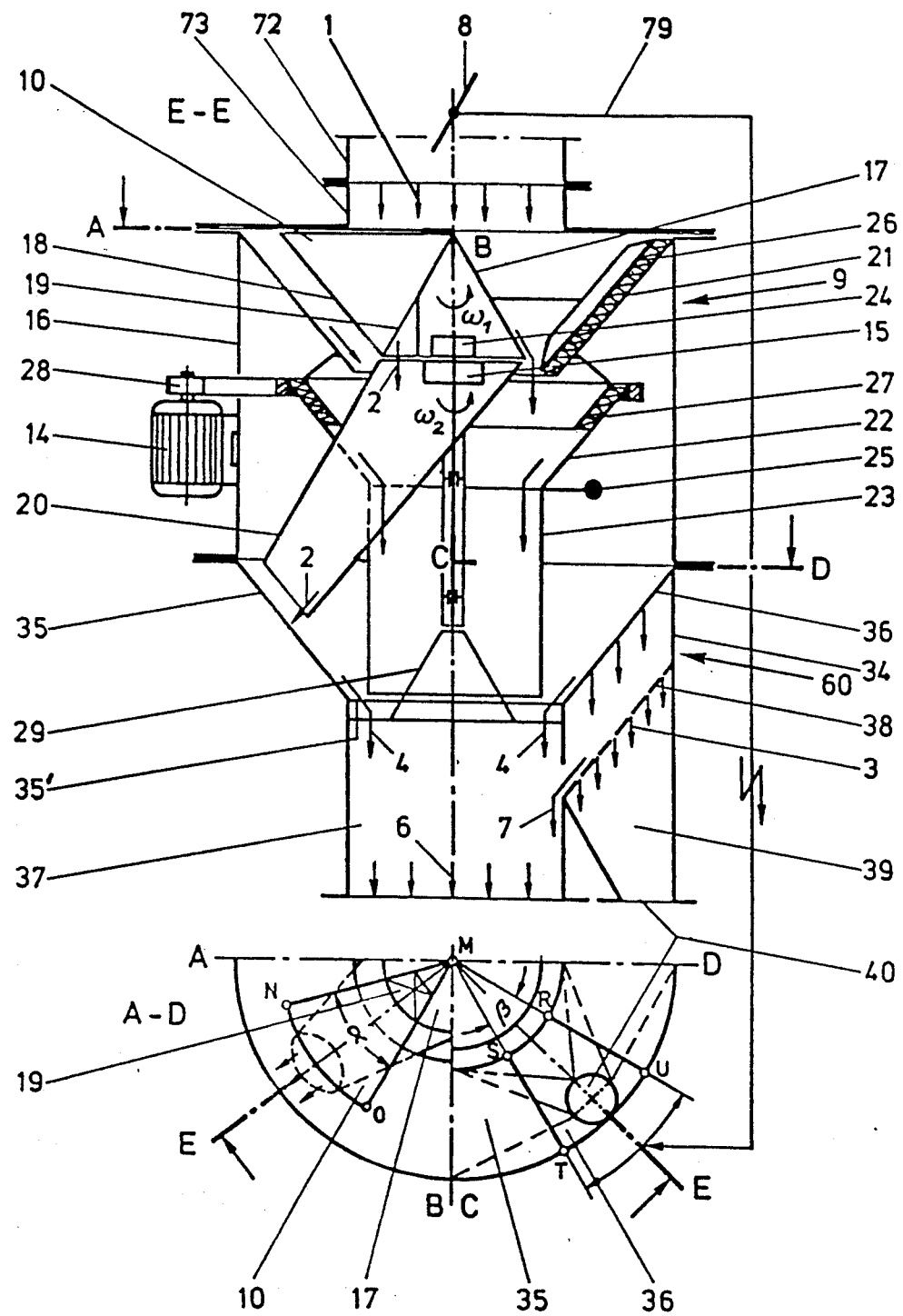
Figure 3:
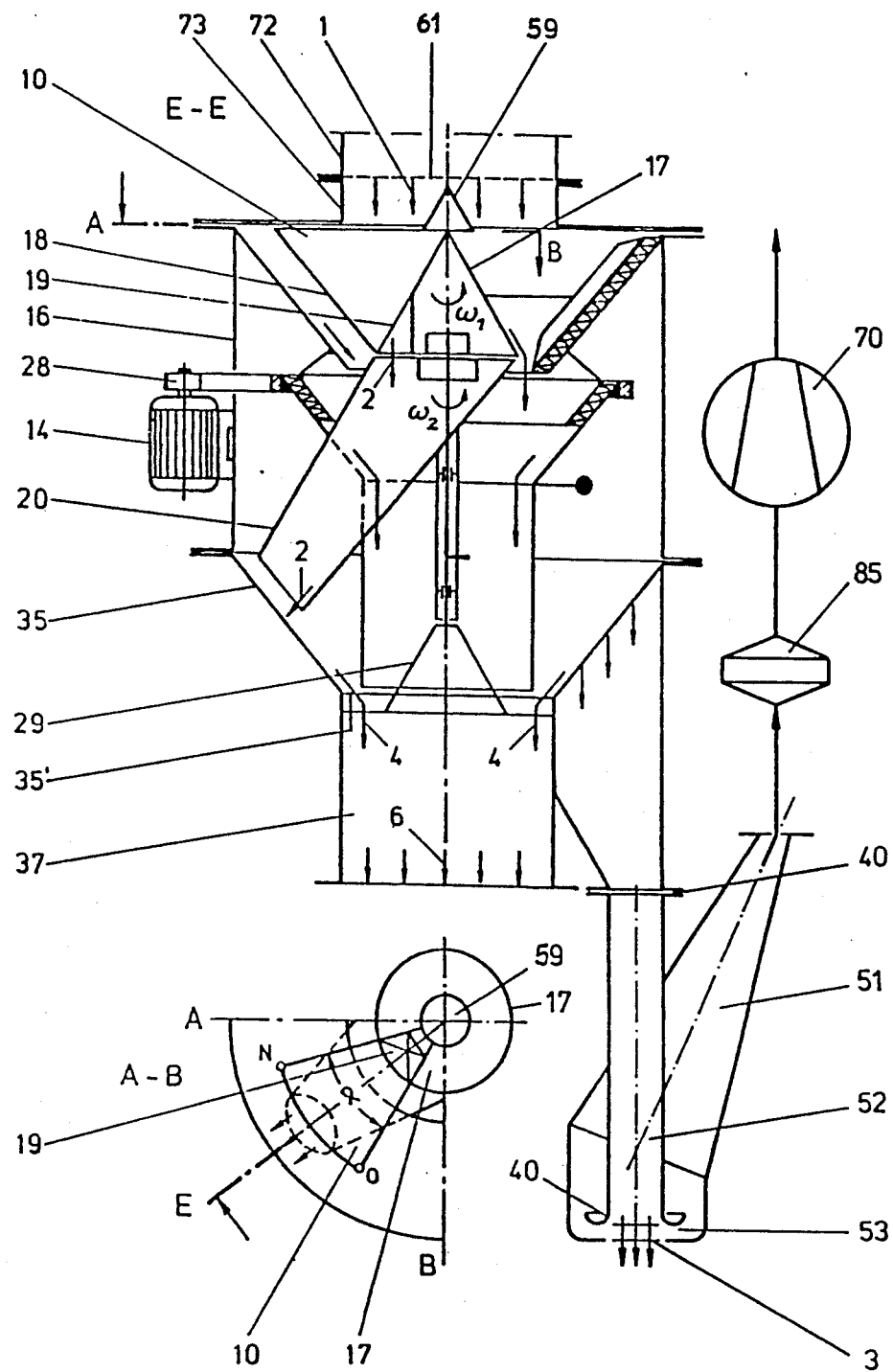
Figure 4:
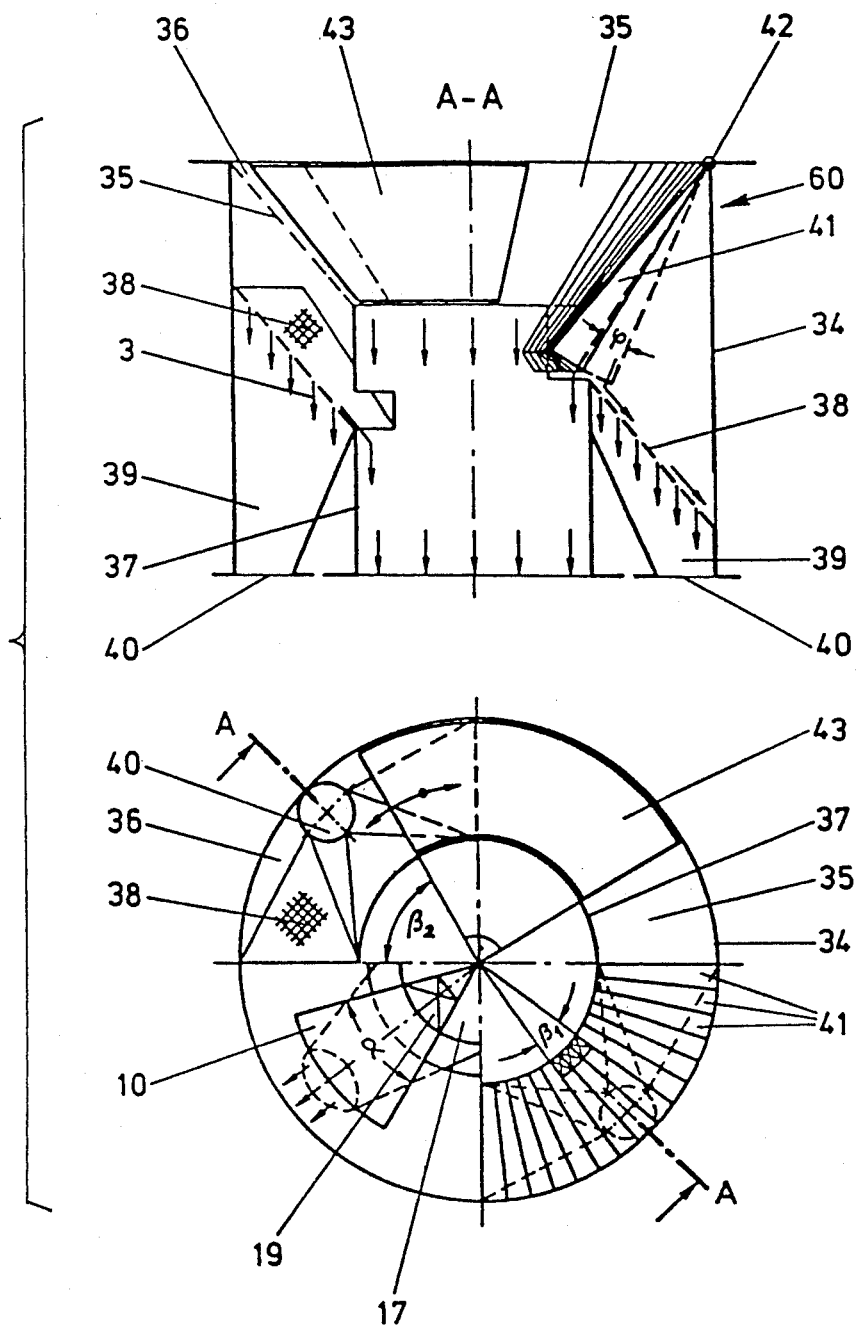
Figure 5:
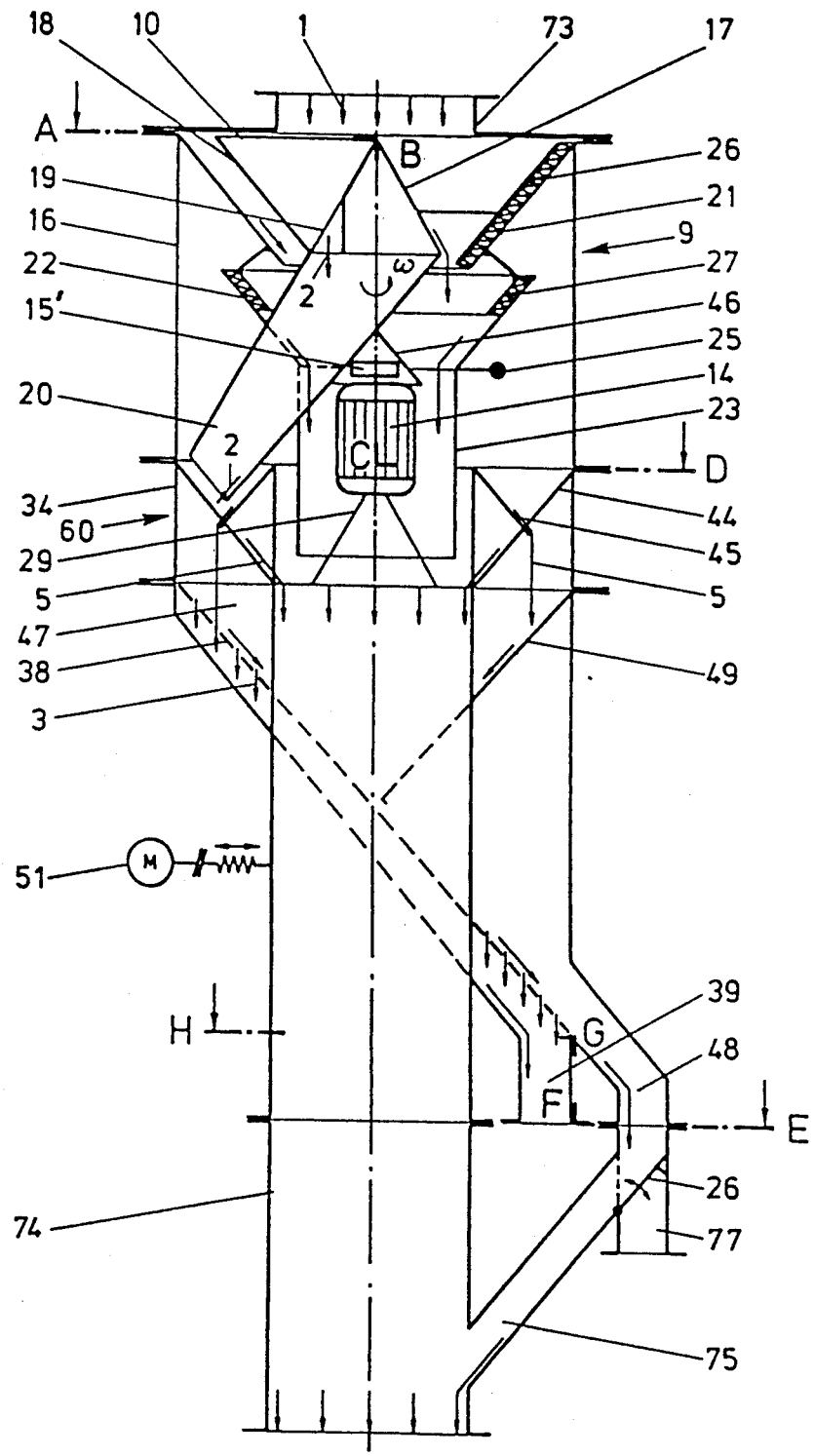
Figure 6:
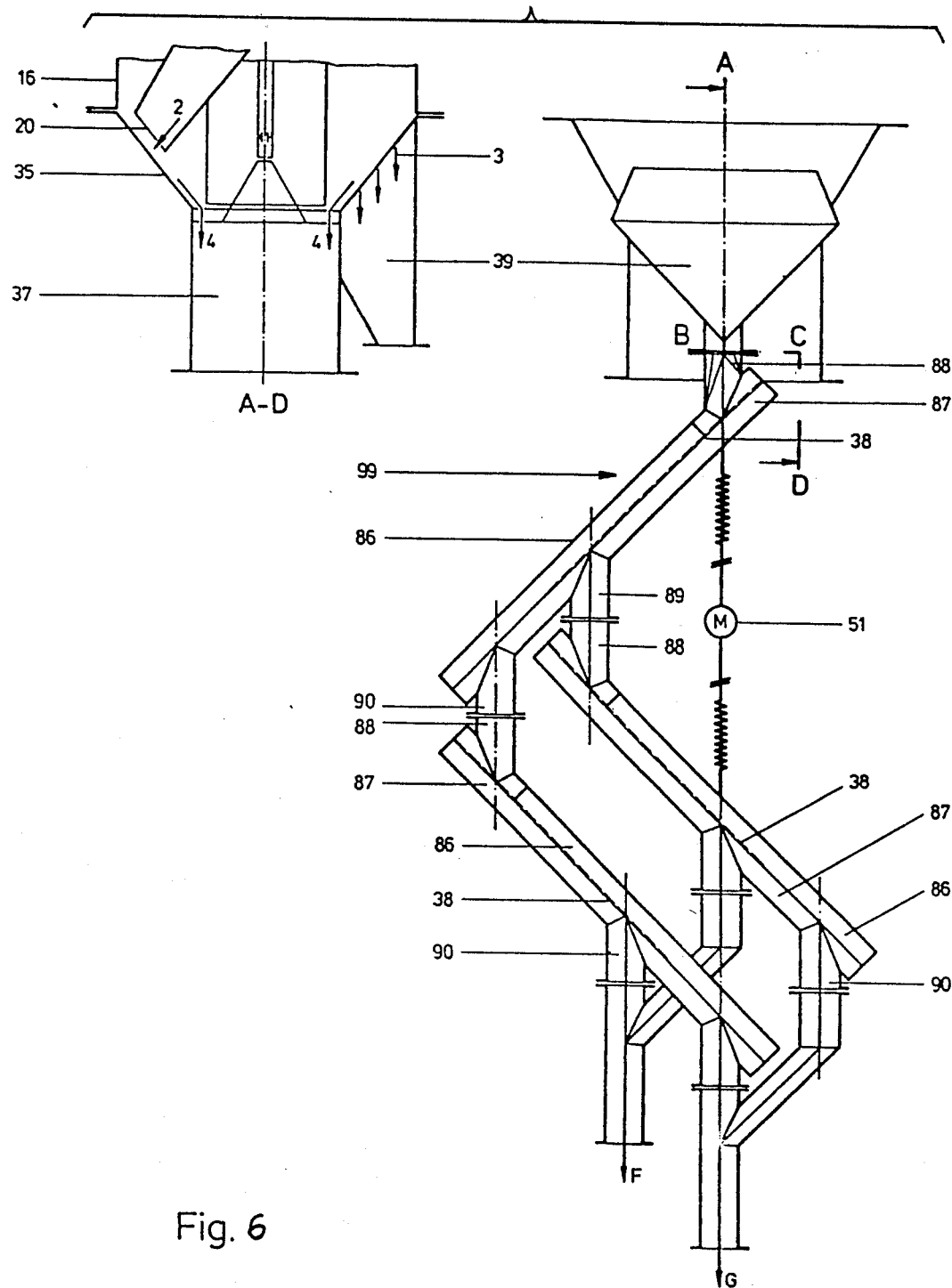
Figure 7:
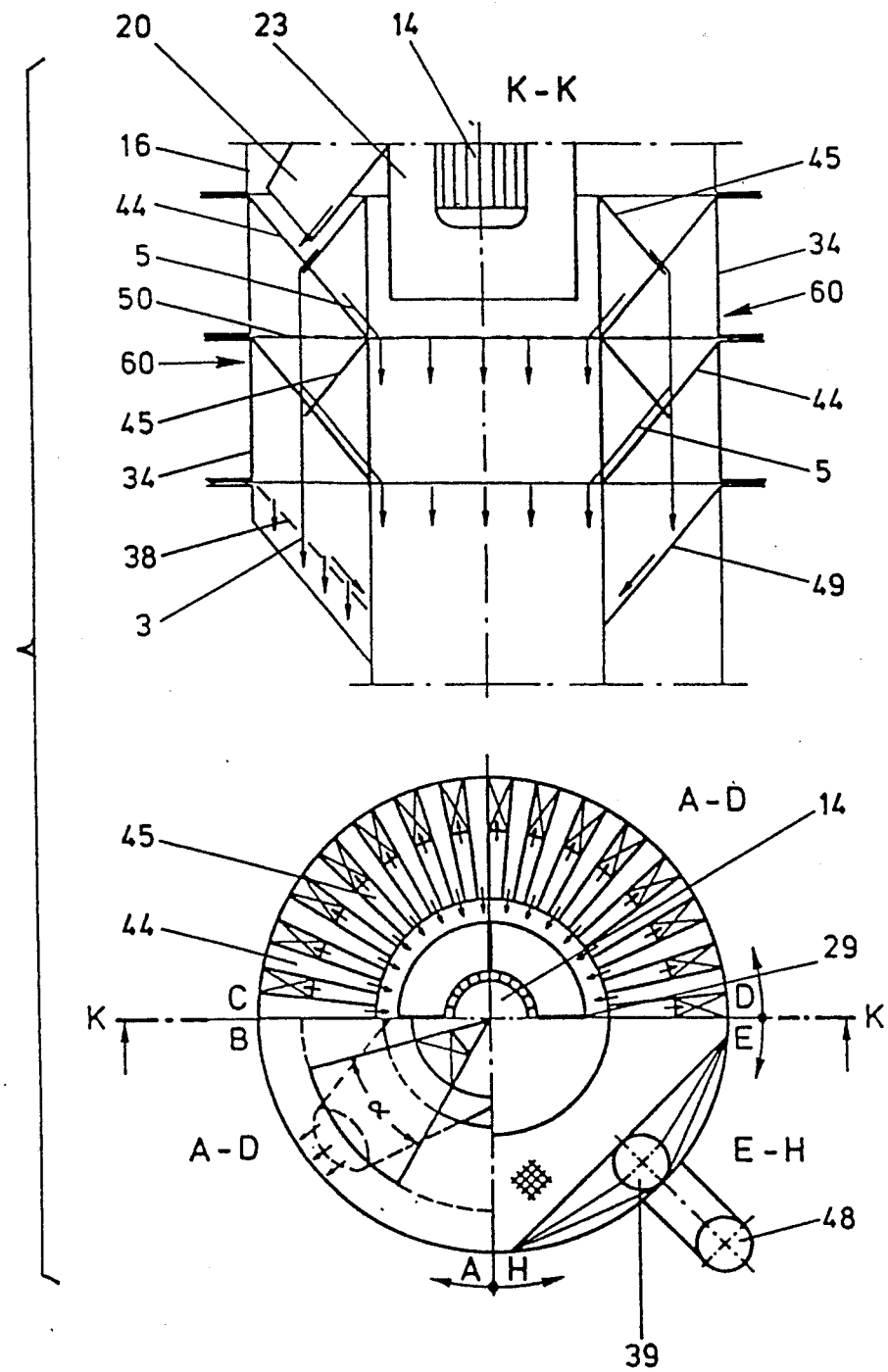

The new apparatus can fundamentally have two different forms. The first form implements the sampling method when the disperse products are contained in fluid transport media, i.e. are conveyed in a carrier medium. The second form implements the sampling of bulk goods in vertical transport conduits or fall shafts in which the product main flow falls freely without transport medium. In the first form in contrast to the second form, with an otherwise fundamentally identical sequence of the sub-steps during the sampling and generating of the sub-flow. It is additionally necessary to ensure the simultaneous identical-velocity (isokinetic) suction extraction of the fluid or carrier medium flow. Examples of embodiment of the new apparatus will be explained with the aid of the drawings, wherein:

FIG. 1 is a sectional view of a first embodiment for sampling and sample splitting of a carrier-medium conveyed product main flow, FIG. 2 is a sectional view of a second embodiment for the sampling and sample splitting of a product main flow falling freely in a vertical transport conduit, FIG. 3 is a sectional view of an embodiment somewhat modified compared with that of FIG. 2, FIG. 4 is a sectional view of two embodiments of the sample splitter according to FIG. 2 for setting the sample splitting ratio, FIG. 5 is a modified embodiment having a sample splitter constructed as chute splitter, FIG. 6 is an embodiment modified compared with FIG. 5 having a different form of the safety screening, FIG. 7 is a sectional view of a further embodiment with in-line series-connected chute splitters as sample splitters.

A first embodiment of the method according to the invention will be explained with the aid of FIG. 1 which shows an apparatus for integrating sampling and in-line sample splitting with simultaneously isokinetic fluid or carrier medium extraction. A product main flow 1 flowing in a transport conduit impinges on a withdrawal or mouth opening 10, formed in this case by a double sector, of a rotatably mounted sampler head 12 of a sampler 9 which with an angular velocity $\omega_1$ slowly rotates about the transport conduit axis and through which a sub-flow 2 is withdrawn from the main flow 1. In the centre of rotation or directly in front of the sampling opening 10 a sensor 11 is provided which supplies the measuring information for setting a suction extraction unit 70, for example a suction fan, for isokinetic extraction of the transport medium.

In the case of sampling from a gas-solid two-phase flow the sensor 11 can be a pressure bore with following capillary conduit which measures the static pressure of the main flow and together with a second pressure bore in the suction tube for measuring the static pressure in the sub-flow furnishes the basic information for isokinetic operation of the sampling by the known principle of differential pressure probes.

When sampling from liquid-solid transport flows the sensor 11 may be constructed as a correlation element with which via the measurement of the particle speeds in the main flow the correct sampling speed for the sub-flow to be extracted can be set. Known constructional forms of correlation measuring points provide in the flow direction two series-connected optical measuring pickups, for example glass fibre sensors, from the signal structure of which by means of a correlation method via the trouble-time displacement the speeds can be deduced.

Behind the double sector of the sampling opening 10 the cross-section of the rotatably mounted rotationally driven sampler head 12 is so formed that a transition cross-section 13 from the rotating sampler head 12 to a stationary cylindrical sampling pipe 30 is circular. From the point of view of production technique this can be simply done with two triangular metal plates which are beaded in the respective symmetry axis and bent through the angle (180-$\alpha$) and connected to the sampling opening in the bend point, being covered by two conical half shells, the half shells joining together at the transition cross-section 13 to give a circular opening.

The stationary extended curved sampling pipe 30 of the sampler 9 conducts the sub-flow 2 from the main flow 1 to an inline sample splitter 60 comprising a cylindrical head piece 31 which rotates in operation and a following cylindrical stator 32. Both the head piece 31 and the stator 32 are divided with stationary fittings in the form of axis-parallel partitions into sector-shaped guide passages 33 which subsequently individually transfer to a concentrator 71 to obtain from the divided sub-flow 2 the analysis sample flow.

The drive of the sampler head 12 and the rotating sample splitter headpiece 31 is by the same drive means 14 (motor M), the transmission ratios being selected so that $\omega_2 > \omega_1$, without being an integer multiple, and $\omega_2$ once again must not be made synchronous with any oscillation in the main flow 1.

The sample splitter 60 comprising a rotating headpiece 31 and stationary stator 32 may also be directly installed together with the concentrator 71 into a main pipe 72 behind the sampler head 12. The drive would then be implemented at the transfer cross-section with different speeds by a common gearing 15.

The concentrator 71 is so constructed that by stepwise combination an analysis sample mass flow 3 necessary for the subsequent use can be preselected and properly set. A remaining residual sub-flow 4 is returned with the extractor unit 70 to the main flow 1 or discarded.

The use of the representatively taken and split analysis sample mass flow 3 is in a measuring path for on-line particle size analysis. After passing a compressed-air-fed impact surface disperser 80 the sample flow is blown as free jet 81 through the measuring zone of a diffraction spectrometer 82. With a catch funnel 83 the widening free jet 81 is intercepted and returned to the main flow 1 either directly or via a separating cyclone 84. The separation in the cyclone 84 coupled with a flow filter 85 permits a conventional checking of the measurement results obtained on-line.

FIG. 2 shows the apparatus for carrying out the method following a transport conduit or a fall shaft with the two sections E—E and A-D.

In the plan view A–D in the left sector AMB a circle sector NMO is seen as rotating sampling opening 10. The sector of a circle includes between its corner points NO the angle $\alpha$. The sector radius MN or MO is made appreciably larger than the radius of the vertical main pipe or fall shaft 72 as clearly apparent in the section E—E in the section line A–B. The diameter difference between the fall shaft 72 and the sample housing 16 is bridged by an intermediate piece 73. With the arrangement illustrated all fall shaft diameters which are less or equal to twice the sector radius MN can be equipped for sampling. The sampling opening 10 is disposed on the entry side of a mouth funnel 18 tapering in the flow direction and serving as sampler head on a hollow deflection cone 17 tapering to a point in the direction opposite to the flow direction and mounted to be driven rotationally. This deflection cone 17 is adjoined by the mouth funnel 18 along a vertical section plane in the lower region. This gives the outlet opening 19 crossed in the plan view A–D. The sub-flow 2 extracted therethrough is transferred to a distributor pipe 20 rotating about the axis of the deflection cone 17 with the angular velocity $\omega_2$. The main mass flow 1 dropping past the sampling opening 10 or the mouth funnel 18 is returned by a stationary first collecting cone 21 to the fall centre and further conducted to a rotatable second collecting cone 22 with adjoining central pipe discharge 23. The distributing tube 20 is fixedly connected to the second collecting cone 22. The latter is set in rotation by a motor 14 via a drive belt 28 with the angular velocity $\alpha_2$. As a result the distributing pipe 20 also rotates with this angular velocity $\omega_2$. The drive is disposed outside the housing 16 so that both the motor 14 and its drive belt 28 do not have any contact with the product. The encapsuling of the drive space between the housing 16 and the fittings 17, 18, 20, 21, 22 and 23 is achieved by the special form of a sealing brush 27 which simultaneously acts as cleaning element between the first or upper collecting cone 21 and the second or lower collecting cone 22. The driven elements 17, 18, 20, 22 and 23 are mounted centrally on a bearing block 29. The drive of the deflection cone 17 and the mouth funnel 18 is via a gearing also serving as connecting element, the lower half 15 of which is installed into the distributing pipe 20 and the upper half 24 of which is installed into the deflecting cone 17, because of the rotation of the lower collecting cone 22. An integrated drive is illustrated in FIG. 5 and will be described with the aid of said Figure. On the outer side of the deflecting cone 17 a cleaning brush 26 is secured which also rotates and keeps the first or upper stationary collecting cone 21 free from depositions on the inside and ensures a constant product flowing off. The cleaning brush 26 is supported by the continuous vibration of the apparatus by means of a vibrator 51 as illustrated in FIG. 5. The rotating cleaning brush 26 lies opposite the mouth funnel 18 and the centrifugal force thereof should be dimensioned so that the eccentric unbalance of the mouth funnel 18 is compensated.

The corresponding centrifugal force 25 for compensating the eccentric unbalance of the distributing pipe 20 is to be provided at the second or lower rotating collecting cone 22. The latter itself is kept free from depositions in the upper entry region by the sealing brush 27 which is supported at the outer face of the first or upper collecting cone 21 and is stationary and does not rotate. In the case of a dust-protected construction the free passage cross-section between the collecting cones 21 and 22 can thus be sealed with a correspondingly rotational symmetrical brush arrangement. This is of particular significance when as illustrated the second collecting cone 22 is rotated from the outside, for example by means of a drive belt 28, and the housing passages and the drive elements are not to come into contact with the product.

Flanged to the sampler housing 16 beneath the section plane CD is a housing 34 of the following in-line sample splitter. The rotating distributing pipe 20 transfers the sub-flow 2 withdrawn to a splitter funnel 35. In the plan view A–D in the sector CMD a splitter opening 36 can be seen in the splitter funnel inner face and is made in the form of a sector and defined by the corner points RSTU. Through this splitter opening 36 with the sector angle $\beta$ between the legs MST and MRU $\beta/360°$ of the sub-flow can fall whilst a remaining residual sub-flow 4 $(1-\beta360°)$ is returned from the splitter funnel 35 through the outlet opening 35' thereof to a lower return pipe 37 to the unextracted main mass flow 6. Secured to the return pipe 37 is the bearing block 29.

Beneath the splitter opening 36 a slightly inclined safety screen 38 is disposed with which coarse grit 7, contaminations or particles lying outside the measuring range of the following sample analyzer can be separated from the analysis sample flow 3 and via the return pipe 37 returned to the main flow 6. The analysis sample flow 3 thus prepared is deflected to a sample dispensing pipe 39 and for the subsequent sample analysis or other use at the shaft transfer opening 40 led out of the combined sampler-sample splitter.

FIG. 3 shows in section E—E a centre rejector cone 59 which is arranged above the deflecting cone 17 in such a manner that it is completely accommodated by the overall height in the intermediate piece 73 and thereabove a coarse-mesh intermediate screen 61 can be installed for uniform cross-sectional distribution of the falling bulk material flow 1. In the quadrant partial section A–B in the plan view the base circles of the superimposed cones 59 and 17 are shown as full circles for clarity.

On transfer of the analysis sample flow withdrawn from the process by means of the sampler and sample splitter it may be necessary to provide at the transfer opening 40 a suction means for dedusting. Such an arrangement is shown in FIG. 3. Disposed round the central transfer pipe 52 is a suction connection 51 such that an adjustable annular gap 53 is formed round the transfer cross-section 40. With a following extractor unit 70 the smallest possible air flow necessary for dedusting is sucked from the outside against and transversely of the fall direction of the analysis sample flow 3 through a filter 85.

For uses in which for example because of varying main mass flows 1 an adaptation of the analysis sample flow 3 must be provided the opening angle $\beta$ is variable and can be set for example in accordance with a mass flow sensor 8. The mass flow actual value is led via a signal line 79 for setting the opening angle $\beta$.

Two embodiments of variable setting means for the sampling angle opening $\beta$ are shown in FIG. 4. In the lower half of the Figure in plan view in the left lower quandrant the plan view illustration of FIG. 2, sector AMB, is repeated. The sampling opening 10, discharge opening 19 and deflecting cone 17 can be seen.

In the lower right quandrant as first embodiment the setting of $\beta_1$ by means of trap chutes 41 is shown. In the illustration the three open chutes at the passage openings are crossed. In section A—A in FIG. 4 at the top right the triangular contour of the trap chutes 41 of U-shaped cross-section can be seen. The opened position is shown in dashed line. In the closed position the open upper edge lies in the plane of the splitter funnel 35. On opening about an outwardly disposed pivot point 42 the trap chute 41 pivots through the angle ψ from the closure position. The analysis sample flow 3 then passes through the safety screen 38 into the sample discharge pipe 39 to the transfer opening 40. When the trap chutes 41 are closed the residual sub-flow 4 returns to the main mass flow 6 through the return pipe 37.

A total of 15 trap chutes 41 is provided in a 90° segment so that at $\beta_{lmax}=90°$ up to 25% of the withdrawn sub-flow 2 can pass the sample splitting. When only one trap chute 41 is opened $\beta_{lmin}=6°$, i.e. only 1.67% of the removed sub-flow 2 is passed on for the further processing as analysis sample flow 3.

The advantage of the trap chute arrangement lies in the simple possibility of combination with digital control means in which by simple yes/no decisions the opening and closing of individual trap chutes 41 can be discretely switched.

A solution for an infinitely variable setting of the analysis sample flow is shown by the two upper quadrants of the lower part of FIG. 4. The sample splitter opening angle $\beta_2$ is set here by the turning of a funnel segment 43. The latter is arranged parallel above or beneath the splitter funnel 35 and can partially or wholly cover the splitter opening 36 of the splitter funnel 35, interrupted over 90°. The sub-flow withdrawn through the remaining splitter opening 36 ($\beta_2$) drops as again shown on the left in section A—A onto the safety screen 38 again before it passes as analysis sample flow 3 via the sample discharge pipe 39 to the transfer opening 40.

The mass flow ratio thus set of analysis sample flow $\dot{M}_A$ to main flow $\dot{M}_H$ is defined by $$\dot{M}_A/\dot{M}_H=(\alpha\cdot\beta) / (360°)^2$$

wherein $\alpha$ is to be fixedly preselected by design such that with the variation $0<\beta<90°$ the mass flow changes $\Delta\dot{M}_H$ of the main flow $\dot{M}_H$ to be expected can be handled.

A modified embodiment of a combined in-line sampler with a following sample splitter is shown in FIG. 5. Here, both the sampler 9 and the sample splitter 60 are modified. The sample splitter here is a rotational symmetrical chute splitter disposed over the entire periphery. The sub-mass flow 2 discharging eccentrically from the distributing pipe 20 is broken down along the entire peripheral path into equisized successive single samples 5 by a stationary circle of chutes of the chute splitter.

The horizontally successive compartments of the chute splitter are so arranged that all the individual samples discarded onto an inwardly inclined long compartment bottom 44 are returned to the main flow and all the individual samples which drop onto an outwardly inclined short compartment bottom 45 are withdrawn as split analysis sample flow 3. Thus, every other individual sample 5 passes to the analysis sample flow 3. The fixed splitting ratio of 1:2 thus obtained is insensitive to mass flow fluctuations from the sampling opening 10 because within a revolution by the integration over the entire cross-section sectoral over or underloads are immediately compensated. For this reason, with this arrangement it is not necessary to operate the sampling opening 10 with a different angular velocity to the following distributing pipe 20 for the transfer to the sample splitter. The constructional solution and the drive in the sampler are thus made correspondingly simpler. The deflection cone 17, mouth funnel 18 with discharge opening 19 and distributing pipe 20 are combined to form a constructional unit which is driven with the motor 14 via a gearing 15' with constant angular velocity ω. The drive via the motor 14 in this case is alternatively from below where it is disposed together with the gearing 15' in protected manner beneath a conical hood 46 entrained in rotation. The driven elements 17, 18, 20, 22, 23, 25, 26 and 46 are rotatably mounted centrally on the bearing block 29.

All the individual samples 5 which are withdrawn via the the short compartment bottoms 45 drop out of the housing 34 of the sample splitter into a flanged collecting container 47 and impinge on the inclined safety screen 38 on the side opposite the sample discharge pipes 39 and the one grit discharge pipe 48. To avoid short-circuit flows the sub-flows of the individual samples are returned from the opposite half space via a deflection chute 49 to the centre of the collecting container 47 and there also directed onto the safety screen 38. This ensures that for all the sub-mass flows an adequately long screen path can be effective before the separated oversize particles or grits are withdrawn through the grits discharge pipe 48 and the screen passage for further use via the sample discharge pipe 39 as analysis sample flow 3. With an additional connecting element 74 via a return well 75 the oversize particles can be returned directly to the product main flow or withdrawn for control purposes from the process via a switch means 79 through a discharge pipe 77.

Another form of the safety screening disposed outside the sampler and sample splitter housing 16, 60 is shown in FIG. 6. With varying grits proportions it may happen that with the arrangement of the safety screen 38 shown in FIG. 5 contaminations or particles outside the measuring range are not adequately separated. A flexible adaptation both to changing amounts and to different separating limits is permitted by the cascade circuit of the simple classifying elements 99 shown in FIG. 6. Each element consists of two half shells. An upper half shell 86 comprises at its upper end an inlet connecting piece 88 which in the uppermost classifying element 99 in the side view of FIG. 6 is flanged directly to the discharge piece 39 of the sample splitter 60.

The analysis sample flow 3 thus taken from the sample splitter and still containing for example grits proportions 7 drops through the inlet connecting piece 88 directly onto the safety screen 38. This screen is clamped between two half shells 86 and 87 and is so dimensioned that the grits proportions are retained as coarse material by the screen whilst the analyzable sample flow 3 passes through as fine material. The coarse material runs off across the safety screen 38 and passes in the lower part of a classifying element 99 to the coarse material discharge pipe piece 90 of a lower half shell 87. The safety screen 38 itself is made shorter than the classifying element 99 and has a length such that a fine material discharge pipe piece 89 of the lower half shell 87 lying further above is completely covered and short-circuit flows are just avoided. The length and steepness of the classifying elements depends firstly on the admissible residence time, which should be as short as possible, and secondly on the necessary sharpness of separation. With classifying elements 99 constructed in this manner easy adaptation is possible thereto and to changing process conditions in that constructionally identical classifying elements 99 are now connected to the discharge pipe pieces 89 and 90 of the first lower half shell 87. This leads both to a rescreening of the fine and of the coarse material of the first stage. Depending on the objective, in these following stages the same or an appropriately adapted screen mesh width may be used. In FIG. 6 the respective fine material of the following classifying elements is combined to give the total fine material F or the analysis sample flow 3 without grits and the respective coarse material is combined to give the total coarse material G or with the grits components by means of suitable Y pipe pieces.

In addition to the embodiment illustrated and described any other combinations of the constructionally identical classifying elements 99 are conceivable. A very clear cut elimination of the grits would for example be achievable with a multiple series connection of classifying elements each at the lower coarse material discharge whilst the fine material could be made up without further subsequent classification from combining the respective passes at the upper fine material discharges. Conversely, a specific clear cut separation of the fine material could be effected.

Another embodiment could be made up with the objective of effecting a multiple classification. For this purpose the mesh widths of the safety screen 38 would have to be appropriately graded in the successive classifying elements.

The mesh widths behind the fine material discharges would have to be progressively smaller and the mesh widths behind the coarse material discharges accordingly larger. A multiple classification following the sampling could for example be used for gravimetric analysis of the profile of a particle size distribution outside the measuring range of a following sample analyzer.

Variants for simultaneous producing of clearly defined classifying cuts and multiple classification can also be connected in combination in series and in parallel.

To support the screening for example a bilaterally acting vibration drive 51 can be installed between the classifying elements.

The partial section A-D in FIG. 6 shows the association of the screen cascade with the illustrations of FIGS. 2, 3 and 4.

FIG. 7 shows in partial sections the plan view A-D and a modified longitudinal section K—K corresponding to FIG. 5.

In the left lower quadrant in the sector AB the plan view illustration of FIGS. 2 and 4 is repeated as a guide. The two upper quadrants CD show the circle of chutes of the chute splitter having the short compartment bottoms 45 and the long compartment bottoms 44 via which the individual samples 5 are returned to the product main flow 1.

From the short compartment bottoms 45 the single samples 5 drop downwardly through the crossed opening trapeziums in the direction of gravity. In the section K—K in addition the variant is shown with which the sample splitting ratio can be adapted. The first splitting stage consisting of the elements 34, 44 and 45 is followed by a second chute splitter arrangement of identical construction. A homogenizing transverse distribution across the cross-section is obtained by a permeable intermediate bottom 50. To be certain the constructional units of the circles of chutes are arranged turned with respect to each other through half a compartment width. This series connection can be repeated k times and thus a sample splitting ratio of $1:2^k$ obtained. The adaptation of the necessary analysis sample flow 3 is effected in this combination by the step number k and the withdrawal angle $\alpha$ in accordance with:

$$\dot{M}_A/\dot{M}_H = (\alpha/360°) \cdot (\tfrac{1}{2}^k) = \alpha/(360° \cdot 2^k),$$

and by the variation of k (only integer) quotas are possible. The arrangement cannot however be used when adaptation to fluctuating or changed main mass flows is necessary in the process operation.

In the quadrant EH of the plan AD the arrangement of the grits discharge pipe 48 and the sample discharge pipe 39 is shown.

I claim:

1. A sampling apparatus, said sampling apparatus comprising:

a vertically arranged sampler housing defining a longitudinal axis therethrough, said sampler housing being connectable to a conduit carrying the products to be sampled so that the products flow by gravity through said sampler housing, said sampler housing defining a first entrance port in a top portion thereof to receive the flow of products from the conduit, said sampler housing further defining a first exit port in a bottom portion thereof connectable to a conduit to permit the flow of products through said first exit port to pass into the conduit;

a sampler head rotatably coupled to said sampler housing about the longitudinal axis thereof, said sampler head being located on the downstream side of said first entrance port to deflect the flow of products therethrough;

a distributing member located downstream of said sampler head and rotably coupled to said sampler housing about the longitudinal axis thereof, said distributing member defining a distributing conduit to receive a first sample flow of products flowing over said sampler head and distribute the first sample flow of products therethrough;

a motor coupled to said sampler head to rotatably drive said sampler head and coupled to said distributing member to rotatably drive said distributing member;

a first collecting member mounted to said sampler housing downstream of said sampler head, said first collecting member defining a second entrance port to receive the remainder of the flow of products over said sampler head, said first collecting member further defining a second exit port to permit the products to pass therethrough and into said first exit port;

a flow splitting member coupled to said sampler housing downstream of said distributing member to receive the first sample flow of products from said distributing member, said flow splitting member defining at least one splitter opening extending therethrough to receive a second sample flow of products from the first sample flow of products flowing onto said splitting member, said flow splitting member including first means for varying the size of said splitter opening during the operation of said apparatus to control the amount of second sample products flowing therethrough, said flow splitting member further defining a third exit port to permit the remainder of the first sample flow of products to pass therethrough and flow through said housing first exit port; and a sampling conduit coupled to said housing downstream of said at least one splitter opening, said sampling conduit defining a third entrance port to receive said second sample flow of products for analyzing the sampled products.

2. Apparatus according to claim 1, said apparatus further comprising:

at least one screen coupled to said housing and mounted downstream of said splitter opening for separating oversized products from the second sample flow of products, said screen diverting the separated products to said first exit port.

3. Apparatus according to claim 1, said apparatus further comprising:

means for vibrating said sampler housing and/or said flow splitting member for facilitating particle movement over the surfaces thereof.

4. A sampling apparatus as defined in claim 1, said apparatus further comprising:

an intermediate screen, said intermediate screen being coupled to said housing upstream of said sampler head to uniformly distribute the flow of products onto said sampler head.

5. A sampling apparatus as defined in claim 1, said apparatus further comprising:

second means for measuring the mass flow rate of products passing over said sampler head and for generating electrical signals indicative of the mass flow rate, said second means being coupled to said first means, and said first means being responsive to said signals for varying the size of said splitter opening in response thereto.

6. A sampling apparatus as defined in claim 1, wherein said motor is coupled to said sampler head and to said distributing member to rotatably drive said sampler head at a first speed ($w_1$) and said distributing member at a second speed ($w_2$).

7. Apparatus according to claim 1, said apparatus further comprising:

an inclined safety screen mounted to said housing downstream of said splitter opening for separating non-analyzable coarse particles from the second sample flow of products.

8. A sampling apparatus as defined in claim 7, said apparatus further comprising:

a shell member coupled to said sampling conduit and in fluid communication therewith, said shell member defining therein a first conduit to receive the second sample flow of products therethrough, said inclined safety screen being mounted to said shell member within said first conduit to separate the non-analyzable particles in the second sample flow.

9. A sampling apparatus as defined in claim 8, said apparatus further comprising:

a first discharge member defining a first discharge conduit therethrough, said first discharge member being coupled to said shell member to receive the second sample flow of products passing through said inclined safety screen; and a second discharge member defining a second discharge conduit therethrough, said second discharge member being coupled to said shell member to receive the portion of the second sample flow that does not pass through said inclined safety screen.

10. A sampling apparatus as defined in claim 1, wherein said sampler head has a substantially conical shape and is oriented so that its tip is facing in the upstream direction.

11. A sampling apparatus as defined in claim 10 wherein said sampler head defines a sampling aperture extending therethrough to receive the first sample flow of products and to pass the first sample flow of products therethrough and into said distributing member, the width of said sampling aperture being defined by an angle (A) measured with respect to the longitudinal axis thereof, and the width of sad splitter opening is defined by an angle (B) measured with respect to the longitudinal axis of said sampler housing.

12. A sampling apparatus as defined in claim 11, wherein said apparatus samples the second sample flow of products ($M_A$) in accordance with a ratio to the flow of products over said sampler head ($M_B$), defined as $M_A/M_B = (A * B)/(360°)^2$.

13. A sampling apparatus as defined in claim 1, wherein said splitting member comprises a substantially conical shaped member located substantially concentric with the longitudinal axis of said sampler housing, said splitter opening being defined through said conical shaped member.

14. A sampling apparatus as defined in claim 13, wherein said first means comprises at least one aperture plate slideably mounted to said conical shaped member and dimensioned to cover said splitter opening, the size of said splitter opening being adjustable by sliding said plate over said splitter opening.

15. A sampling apparatus as defined in claim 13, wherein said conical shaped member defines a sampling aperture extending therethrough, and said first means includes a plurality of chute members, each of said chute members being pivotally mounted on one end to the downstream side of said conical shaped member, and the other end of said chute member defining a free end said chute members being dimensioned to cover said sampling aperture such that said chute members may be pivoted toward or away from said sampling aperture, said splitter opening being defined by the space between the free ends of said chute members pivoted away from said sampling aperture and the adjacent edge of said conical shaped member defining said sampling aperture.

16. A sampling apparatus as defined in claim 15, wherein said first means is adapted to adjust the width of said splitter opening about equal to the arc of an angle (B), by pivoting said adjacent chute members that are substantially equal in overall width to the arc of the angle (B) away from said conical shaped member.

17. A sampling apparatus as defined in claim 15, wherein said sampling aperture extends through an angle less than 180° within said conical shaped member, wherein said angle is measured with respect to the longitudinal axis of said sampler housing.

18. A sampling apparatus as defined in claim 1, said apparatus further comprising:

a drive shaft journaled to said housing and extending along the longitudinal axis thereof, said distributing member being rotatably driven by said drive shaft.

19. A sampling apparatus as defined in claim 18, wherein said distributing member comprises a hollow tubular portion defining said distributing conduit therethrough, said tubular portion being coupled to said drive shaft and defining a fourth entrance port on its upstream end and a fourth exit port on its downstream end, said fourth entrance port receiving the first sample flow of products flowing over said sampler head and said fourth exit port permitting the first sample flow of products to flow therethrough onto said flow splitting member.

20. A sampling apparatus as defined in claim 19, wherein said first collecting member is coupled to said drive shaft and to said motor, and said motor rotatably drives said first collecting member about said drive shaft.

21. A sampling apparatus as defined in claim 20, wherein said tubular portion of said distributing member is coupled to said first collecting member, and said tubular portion is rotatably driven with said first collecting member.

* * * * *